United States Patent [19]
Duret et al.

[11] Patent Number: 5,143,086
[45] Date of Patent: Sep. 1, 1992

[54] DEVICE FOR MEASURING AND ANALYZING MOVEMENTS OF THE HUMAN BODY OR OF PARTS THEREOF

[75] Inventors: Francois Duret, Le Grand-Lemps; Jean-Louis Blouin, Vienne, both of France

[73] Assignee: Sopha Bioconcept S.A., Vienne, France

[21] Appl. No.: 548,948

[22] PCT Filed: Nov. 17, 1989

[86] PCT No.: PCT/FR89/00593
§ 371 Date: Jul. 27, 1990
§ 102(e) Date: Jul. 27, 1990

[87] PCT Pub. No.: WO90/05484
PCT Pub. Date: May 31, 1990

[30] Foreign Application Priority Data
Nov. 18, 1988 [FR] France ............... 88 15484

[51] Int. Cl.⁵ .................................. A61B 5/103
[52] U.S. Cl. .................................. 128/777; 433/69
[58] Field of Search ............ 128/777, 782; 433/68, 433/69; 356/141, 152

[56] References Cited

U.S. PATENT DOCUMENTS

| | | | |
|---|---|---|---|
| 4,258,229 | 3/1981 | Eggert et al. | 128/773 |
| 4,303,077 | 12/1981 | Lewin et al. | 128/777 |
| 4,411,622 | 10/1983 | Hansen | 128/777 X |
| 4,447,207 | 5/1984 | Kataoka et al. | 128/777 |
| 4,547,154 | 10/1985 | Puschmann | 433/49 |
| 4,673,352 | 6/1987 | Hansen | 433/69 |
| 4,687,003 | 8/1987 | Burckhardt | 128/777 |
| 4,836,778 | 6/1989 | Baumrind et al. | 433/69 |
| 4,859,181 | 8/1989 | Neumeyer | 433/69 |

FOREIGN PATENT DOCUMENTS 3807578 9/1989 Fed. Rep. of Germany ...... 128/774
175545 10/1983 Japan .

OTHER PUBLICATIONS

"Recording of Mandibular Movements by Intraorally Placed LED's", Karlsson, vol. 35, Acta. Odont. Scan., 111 (1977).

Primary Examiner—Max Hindenburg
Attorney, Agent, or Firm—Herbert Dubno

[57] ABSTRACT

A device for determining mandibular motion wherein three light emitting diodes at the vertices of a triangle are temporarily fixed to teeth of the subject, the light emitting diodes are sequentially energized, and two sensors responsive to the light emitting diodes are mounted on a headpiece applied to the head of the subject and are trained on the light emitting diodes.

17 Claims, 5 Drawing Sheets

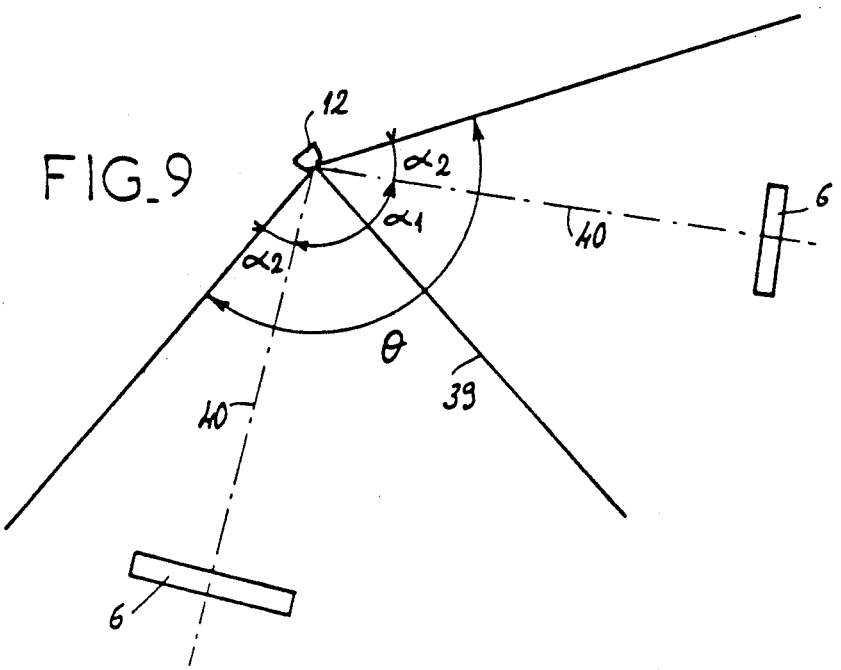
FIG.9
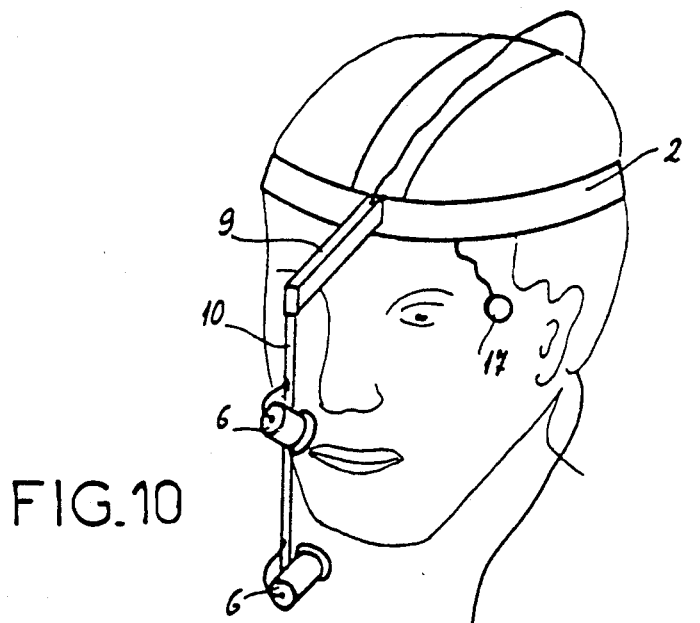
FIG.10
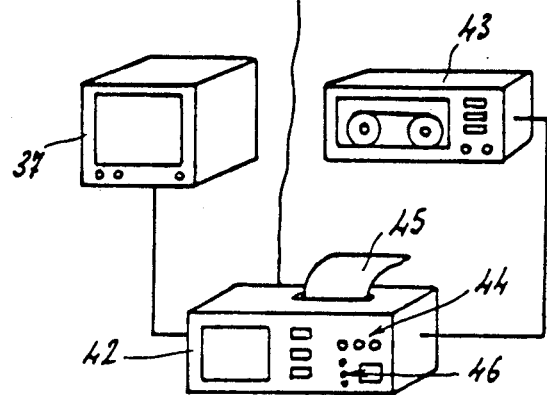

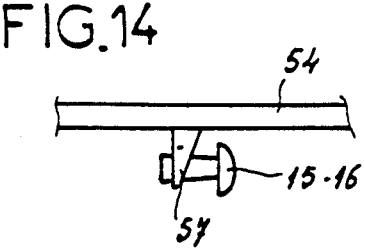
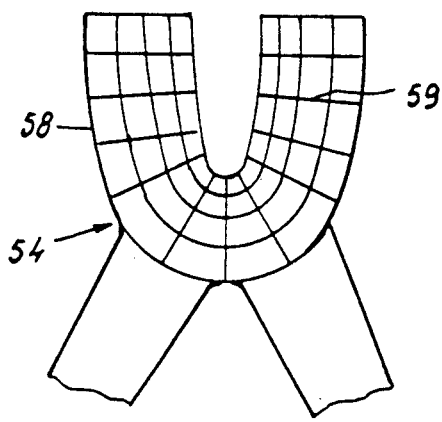
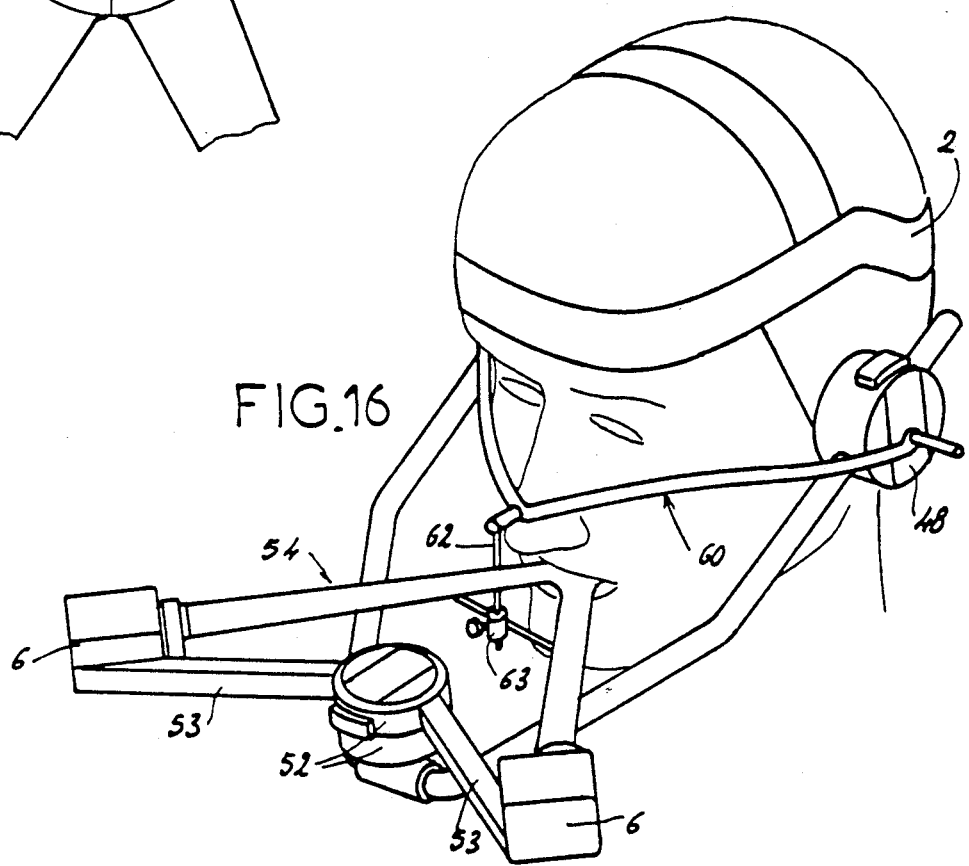
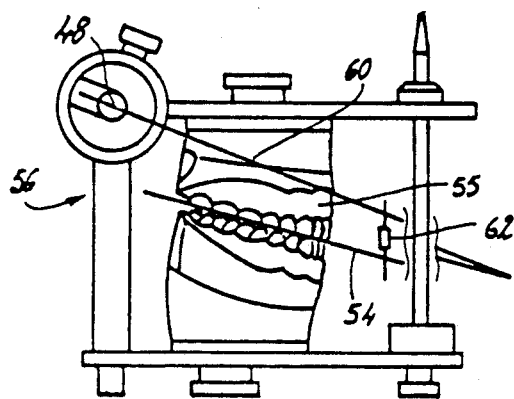

DEVICE FOR MEASURING AND ANALYZING MOVEMENTS OF THE HUMAN BODY OR OF PARTS THEREOF

CROSS REFERENCE TO RELATED APPLICATIONS

This application is a national phase of PCT/FR 89/00593 filed Nov. 17, 1989 and based, in turn, upon French national application 88 15484 filed Nov. 18, 1988 under the International Convention.

FIELD OF THE INVENTION

The present invention relates to a device for measuring and analyzing the movements of the human body by electronic means and in particular, the measurement of the mandibular movements with the aim of permitting simpler and more accurate production of prostheses, rapid diagnosis of articular pathologies, and transmission of data which can be used directly in a computer-aided design and manufacture technique in the field of dentistry, such as described in French Patent No. 82/06,707.

BACKGROUND OF THE INVENTION

The various methods prevalent up to 1985 for analyzing mandibular kinematics were based on the use of mechanical instruments all to a greater or lesser extent derived from mandibulographs, whose commercial appearance dated from the 1950s.

Such apparatus permitted the recording of a relatively restricted expression of these kinematics, since the expression was limited to the so-called border movements of the mandible. Moreover, the interpretation of the graphs obtained by these methods gave rise to a number of errors due to the misunderstanding of the functional cycle and to the intervention of mechanical processes which led to the existence of artifacts in the graphs.

Another negative aspect of such apparatus is the considerable space taken up in the oral cavity in cumbersome and bulky fixation procedures with which it was impossible to envisage the recording of a normal physiology of the said kinematics.

The use of apparatuses employing a recording system, which occupies little space in the oral cavity and does not in any way interfere with the masticating cycle, nowadays permits the straightforward recording of the functional kinematics which have up till now been remote from our everyday concerns.

The work carried out by Lundeen and Gibbs had already provided a first example of this with the "gnathic replicator". These studies have been added to considerably by a large number of authors, who have demonstrated the more uncertain aspects of the masticating cycles and have permitted a more exact approach to the phenomena which intervene in the cycles in term of neuromusculature, quality of the foods crushed, posture of the subject etc.

A number of other apparatuses have attempted to represent as clearly as possible the data essentially characteristic of the masticatory apparatus. Mention should be made in particular of the recent work carried out by Lewin, which has led to the production of the Siemens "sirognathograph", the "Nex K6 diagnostic system" from Myo-tronics Inc, the "LR Candylograph" from Dentron, the "stereognathograph" from Dr. Burchhardt or the Cyberhoby computer pantograph from Denar.

Finally, mention should be made of the "visitrainer" described for the first time in 1981 by the team under Professor Hobo and Professor Mori in Japan. It uses an LED (light emitting diode) fixed on the mandibular incisors. At the same period the team under Professor Hobo developed a system using a charge transfer device (CTD) as a reading means; the whole assembly is connected to various calculation elements (computer) and their associated peripherals.

These works include the principles developed by Barrie in 1967 and his "photoelectric mandibulography". 1984 saw the appearance of the first "Saphon visitrainer model 1". The latter will soon be followed by the C2 model, then the 3 (SVT) model. These models have been developed by the company Tokyo Shizaisma C.O. Ltd. and differ in particular in their ergonomic approach (weight, number of points analyzed per second, etc. . . . ).

The fact of having to move a single camera three times in order to analyze the movements in the horizontal, frontal and sagittal planes prevents these movements from being determined spatially, because a subject never moves his joints in the same manner, and this prevents any connection from being made between the three movements.

At the same period Jemt and Karlson showed that the use of two cameras and a diode fixed on the incisors could permit analysis of the mandibular movements in three dimensions. In actual fact, this is not correct. In particular, it is found that a purely rotational movement, often present in the human body, cannot be detected correctly.

OBJECTS OF THE INVENTION

An object of the present invention is to overcome these disadvantages by providing analyses in three dimensions, adapted to all odontological and medical applications, by specifying the means permitting analysis of the movements, and by providing a signal which can be analyzed directly by a computer, and this in a very rapid manner, while at the same time affording the possibility of verification of the analysis, without any intermediate manual action, as constituted hitherto by the moving of the cameras.

Another object of the invention is to provide an apparatus which is economically attractive for the purpose described and is applicable to a wide market and which can afford a real saving in time and manpower.

SUMMARY OF THE INVENTION

The device to which the invention relates comprises:
a set of three light emitting diodes fixed in a removable manner on that part of the body whose movement is to be analyzed,
two sensors designed to follow the movements of the diodes and mounted on a fixed support in such a way that the diodes are located in their field,
and means for controlling the lighting of the diodes, the functioning of the sensors and the processing of the data supplied by the latter.

The light emitting diodes advantageously emit in the infrared range and have an angle of emission of the order of 180°. The light emitting diodes emit at a wavelength of 900 mm, with a power of approximately 30 mW. In the case where the movements of a jaw are being detected, the diodes, which are fixed for example on the incisors, have the advantage, since they emit in the infrared range, of having a certain immunity with regard to the ambient light and of permitting detection when the lips are closed.

In addition, the angle of emission of 180° permits the simultaneous tracking of the movements by the two sensors. The sensitivity of the sensors is in the region of 900 mm. The overall sampling frequency being from 1 to 2 KHz for a recording period of 20 seconds, the resolution obtained is substantially greater than that observed with the other apparatuses described.

This device has synchronization means providing for the successive lighting of the three diodes for brief intervals of time and for the simultaneous functioning of the sensors.

In addition, this device comprises two signal-shaping stages permitting the preparation of the data and the transmission thereof for digitalization, a digitalization stage providing for the analog-digital conversion of the signal, under the control of the synchronization means, and a storage stage permitting storage of the data and visual display thereof on a graphic monitor. It should be noted that an external communication bus permits transmission of all the data to the CAD/CAM system.

The three light emitting diodes are advantageously arranged at the three points of a triangle. The positioning of these three diodes makes it possible to meet the requirements for simultaneous recording of the movement of a point of the mandible relative to three planes which are currently used in dentistry, namely the horizontal plane or occlusal plane, the frontal plane and the sagittal plane.

BRIEF DESCRIPTION OF THE DRAWING

The invention will be better understood in any case from the description which follows and in which reference is made to the attached diagrammatic drawing showing, by way of non-limiting examples, several embodiments of this device:

FIG. 9 shows the optical trajectory of the measurement;

FIG. 10 is a highly diagrammatic perspective view of the whole installation;

FIG. 14 is a partial side view of the fork in FIG. 13;

FIG. 15 is a partial plan view of the fork in FIG. 13;

FIG. 16 is a perspective view of equipment complementing the device in FIG. 12; and FIG. 17 is a side view of an articulator.

SPECIFIC DESCRIPTION

Figure 1:
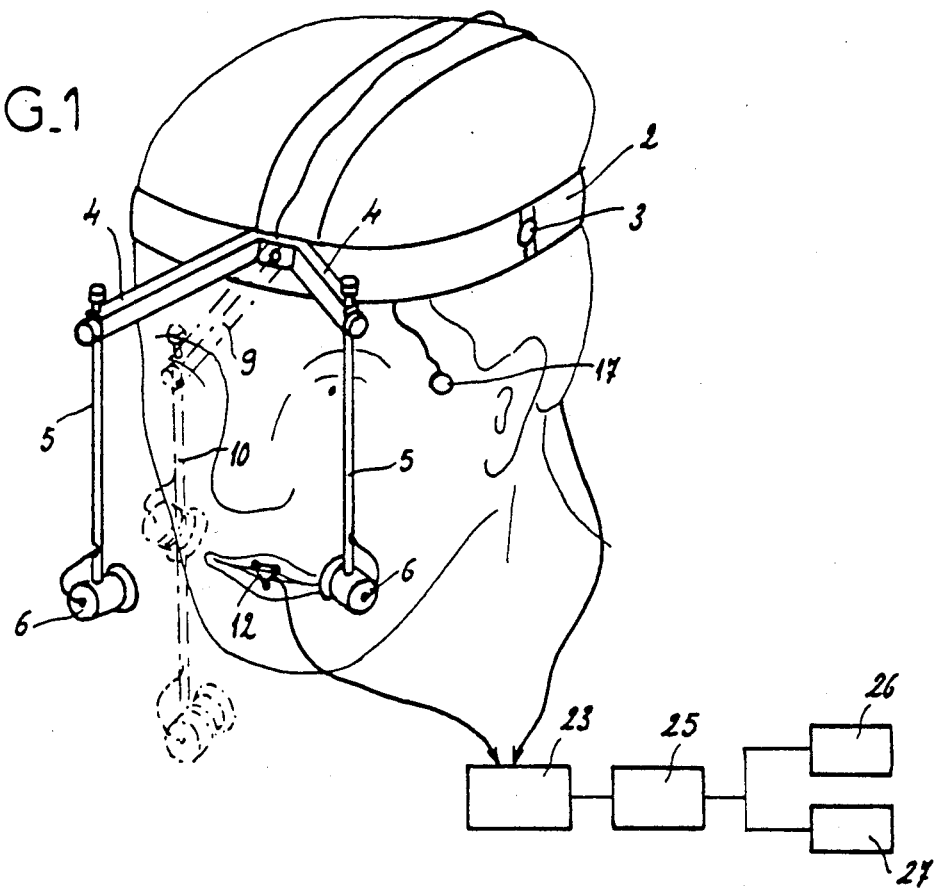
FIG. 1 is a perspective view of a first imaging device.

The various devices shown in the drawing are designed for measuring the displacement and analyzing the movements of a jaw. The patient is fitted with a headpiece 2 provided with means 3 for adjusting its size. On the front face of the headpiece there are fixed two substantially horizontal and diverging arms 4, at the free end of each of which there is mounted a substantially vertical rod 5 fitted, at its lower end, with an infrared sensor 6 forming a camera. The position of each sensor 6 can be adjusted both in the direction of the arm 4 and in the direction of the corresponding rod 5 by means of screws 7, 8, respectively. The arms 4 are positioned in such a way that the cameras form between them an angle of between 35° and 120°, and preferably 90°.

Figure 6:
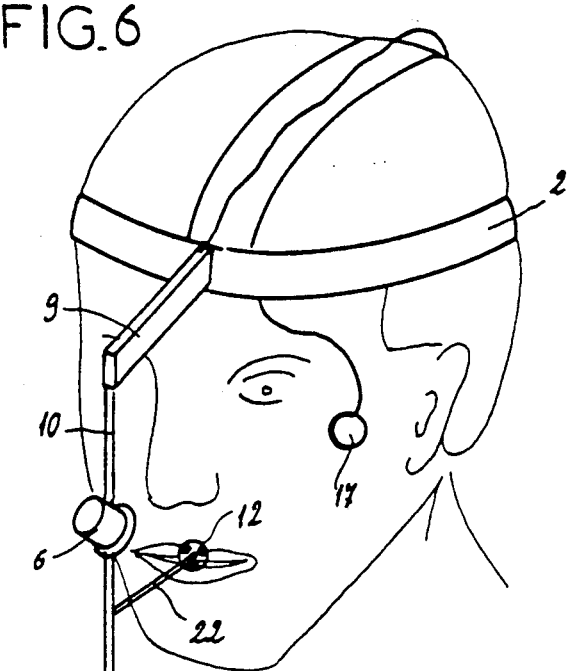
FIGS. 5 and 6 are two views corresponding to FIGS. 3 and 4 respectively, showing the device for calculating the distance between the diodes and the receiver, in a second embodiment.

In one variant, shown with dot-and-dash lines in FIG. 1, as well as in FIGS. 6 and 10, the two sensors 6 are supported on a single arm 9 and single rod 10, which simplifies the adjustments and limits the size.

Figure 2:
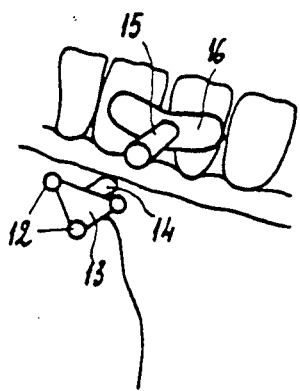
FIG. 2 is a perspective view, on an enlarged scale, of part of the dental arch and of the device for fixing the diodes on the latter.

This device comprises three light emitting diodes 12 which emit in the infrared range and are fixed on a single support 13 and arranged at the three points of a triangle. This support 13 is very rigid in order to prevent a relative movement of the diodes 12 during the displacement of the organ on which the support is fixed. This support 13 is fixed to a rod 14 (FIG. 2) designed to be engaged in a tubular element 15 fixed to a support plate 16 designed to be fixed in a removable manner on the teeth. This fixation is obtained using a photopolymerizable cement. The diodes are fixed on the teeth in two stages: first the support 15, 16 is fitted on the teeth; then the diode support is forced on this assembly, with stabilization by wedging, by a magnet or else by a spring action.

A sound sensor 17 permits detection of the moment at which the teeth come into contact and separation of each cycle comprising a mastication.

In order to have an exact relationship between the displacements and their representation, before carrying out the measurements a graduated rule is placed between the diodes 12 and the cameras before definitively fixing the position of the latter. The position of the cameras is adjusted by acting on the screws 7, 8.

Figure 4:
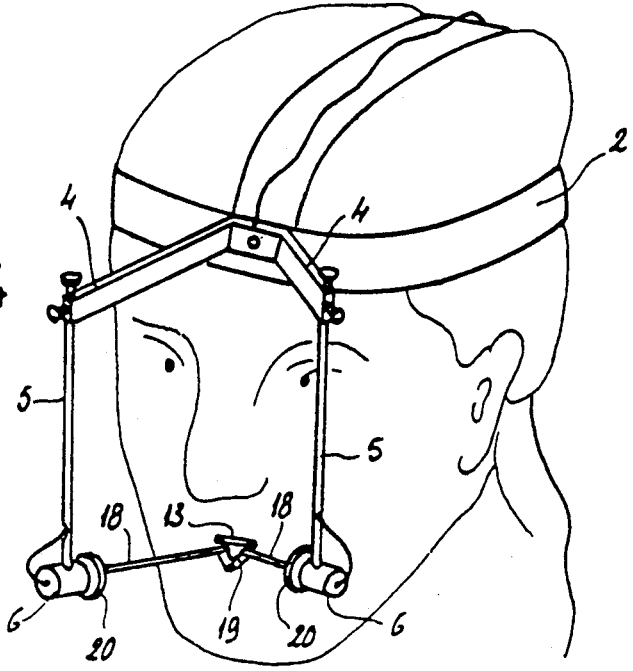
FIG. 4 is a highly diagrammatic perspective view showing the use of the device in FIG. 3.
Figure 3:
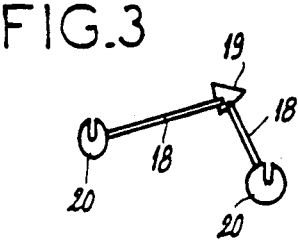
FIG. 3 is a perspective view of a device for measuring the distance between the sensors and the diodes.
Figure 5:
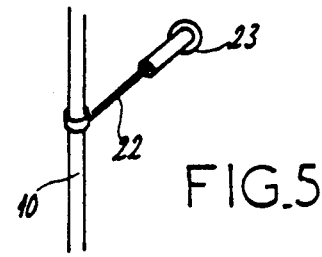

In the embodiment shown in FIG. 3, the device for calibrating the distance comprises two rods 18 connected to one another by a plate 19 designed to bear against the diodes, each rod 18 being fitted at its other end with a plate 20 designed to bear against the camera. The use of this calibration is shown diagrammatically in FIG. 4. FIGS. 5 and 6 show the calibration method in the case where the two sensors 6 are supported on a single arm. In this case, only one rod 22 is provided, for example mounted slidably on the vertical rod 10 and fitted at its free end with a single bearing plate 23.

The data supplied by the cameras are transmitted to an electronic unit 24 and processed in an analysis unit 25, with possible connection either in the framework of a computer-aided control 26 or a conventional imaging 27.

The assembly of cameras and diodes is under the control of several electronic and data processing stages, which are:

A signal-shaping stage permitting the summation of the succession of analysis points in the two planes of the cameras. It is in fact important to have the overall shape of the curve, and not the orientation of one point.

This stage functions as follows:
reception of the signal,
current/voltage conversion,
voltage input on four differential inputs by diodes,
analog-digital conversion,
input on a computer and, if appropriate, a link to a CAD system.

Figure 7:
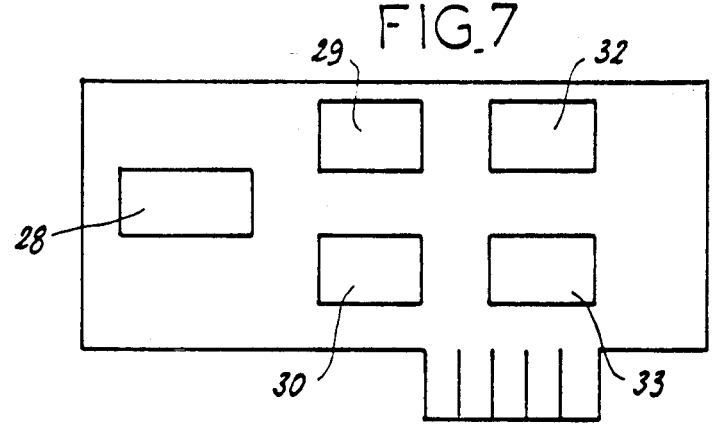
FIG. 7 is a view of a card for processing the signals.

A calculation stage permitting, by means of appropriate software, transformation of the curves analyzed on the two planes of the camera in projection to the three planes of the face used in dentistry, namely the horizontal plane or occlusal plane, the frontal plane and the sagittal plane. The electronic card used is shown in FIG. 7 and comprises a memory 28, a memory/conversion interface 29, a memory/central unit interface 30, a conversion system 32, and a system 33 for synchronization of the signals.

Apart from the cards whose functions have already been described, mention should be made of the presence of a memory permitting storage of the information arriving in the form of points, in order to construct the curves, and in particular of the synchronization by means of which it is possible to light each diode 12 successively and to indicate, for each sensor 6, which diode is emitting at the moment the light point is received.

It is thus possible to receive the respective trajectories of the three points on each sensor 6. It is from these six curves that the three curves specific to the movement are built up and then referred to the three known dental planes.

Figure 8:
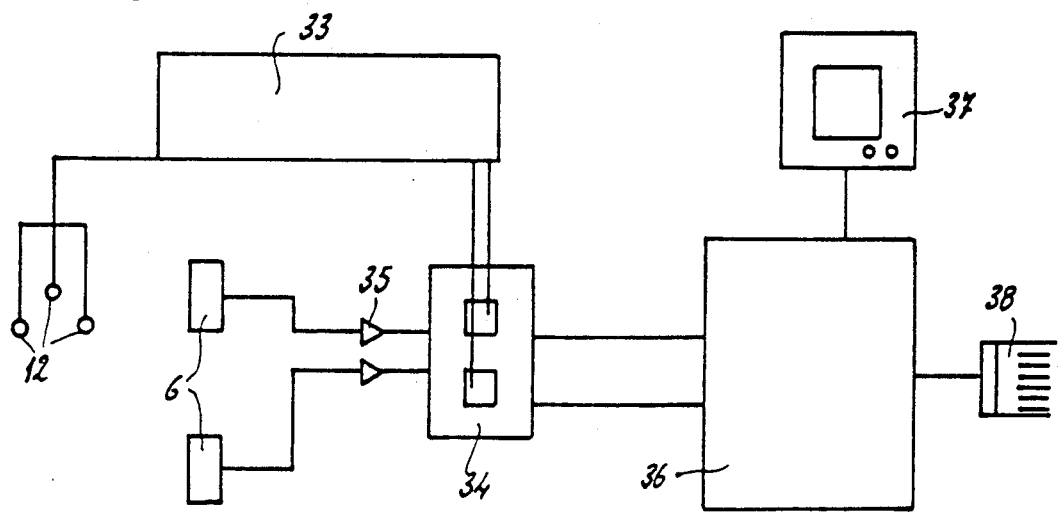
FIG. 8 is a block diagram of the installation.

FIG. 8 shows the overall system in which the various elements are designated by the following references:

The diodes 12 are under the control of the synchronization system 33. This system is also connected to the digitalization stage 34 to which the two sensors 6 are connected by way of a formatting stage 35. The digitalization stage is connected to the central unit 36, to which there are connected a visual display screen 37 and a transmission stage designated by general reference 38.

As is shown in FIG. 9, the principal axis of emission of a diode 12 has an angle of emission $\theta$ equal to $\alpha 1 +- 2\alpha 2$ where $\alpha 1$ is the angle formed by the orthogonal optical axes 40 of the two sensors 6 and where $2\alpha 2$ is the angular aperture angle of the optics of the sensors.

The two sensors each define a plane reference line, the two reference lines thus obtained forming with the plane of the diodes a trihedron making it possible to locate each emitting diode spatially. If this trihedron is a straight line trihedron, the subsequent correlation calculations are eliminated. If one emitting diode defines the movements, except for the centered rotation, two emitters cannot detect the rotation about the axis of each emitter, while the use of three emitters permits the detection of all the movements of translation and of rotation.

By way of example, the following values can be used:
duration of recording 20s,
overall sampling frequency 1 KHz,
number of gross samplings 20,000,
number of secondary samplings (3 per gross sampling) 60,000,
four coordinates per secondary sampling 240,000,
number of octets per coordinate: 2,
total number of octets: 480,000.

Between 2,000 and 4,000 values are obtained per cycle of 1 second, which represents an accuracy 10 to 20 times greater than that of known apparatuses.

In practice, the headpiece 2 is placed on the head of the patient before fixation of the sensors 6 and calibration by means of the adjustment devices 7, 8. The assembly is connected to a computing system including the analysis card and comprising in particular an oscilloscope 42, a monitor 37 and, if appropriate, a video recorder 43. The diodes 12 are illuminated alternately and their signal is received by the sensors 6. At the start of the analysis, the jaw of the patient is in a tight occlusion position. The apparatus is started up, after which the patient is asked to carry out a set of movements which it is possible to display visually either in an overall fashion or at the level of the various planes on which the image is projected by selection using the various buttons 44. These data can be simply visually displayed or printed out on paper 45.

Moreover, certain additional information, such as angle calculation, amplitude of movement, time of cycle, can be provided by selection of buttons 46.

A direct connection to a CAD/CAM device (computer-aided design/computer-aided manufacture) can be used, as described in particular in French Patent 82/06,707. A dental prosthesis can be constructed by means of an optical impression, mathematical surface production of the experimental model as a function of this impression, and direct working. The fact that a wax model is not used makes it necessary to work on rough surfaces on screen, which prohibits the use of traditional dental articulators.

According to another of its aspects, the present invention makes it possible to transcribe to the surfaces modeled statically the dynamic movement when the patient moves his limbs or his jaw. This makes it possible, on the one hand, to alter certain angles or surfaces which could act adversely, but also to develop surface equations integrating the concept of time.

In order to obtain data on the planes separately or together, without knowing the spatial development and ignoring the possible pure rotations, the system according to the invention affords the possibility in its electronic circuit of being able to follow only one diode. This analysis is ensured by a perfectly parallel construction of the components and circuits and by an access to the clock system.

Figure 11:
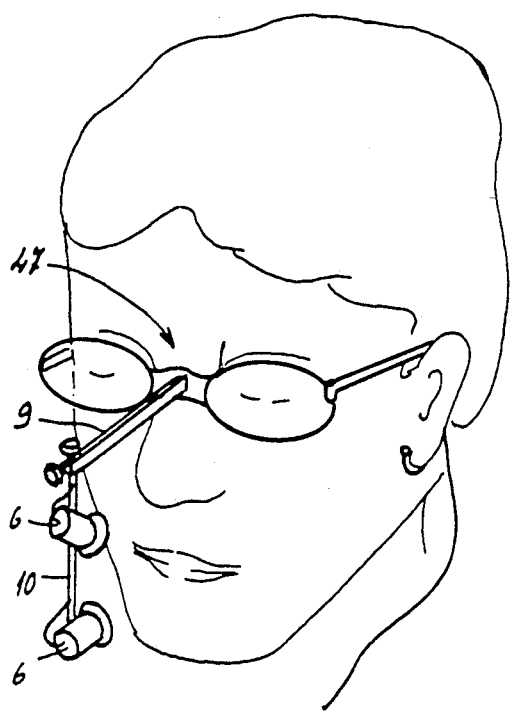
FIG. 11 is a view of a variant of the device for supporting the receivers.

FIG. 11 shows an embodiment for the sensor-supporting device described above, in which the same elements are designated by the same reference numbers. In this case the system, instead of consisting of a headpiece, consists of adjustable spectacles 47 worn by the patient.

Figure 12:
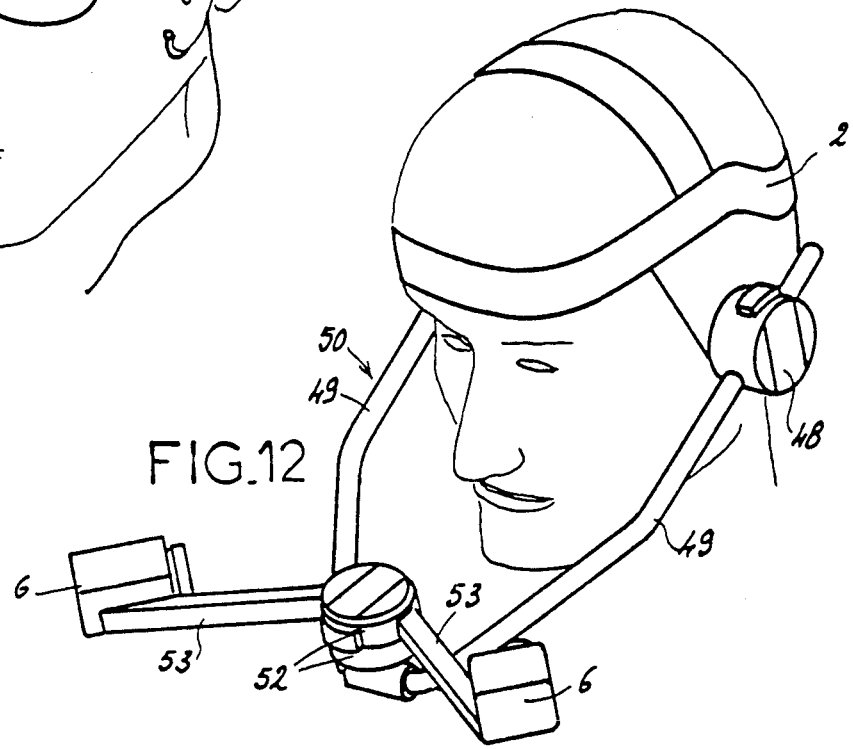
FIG. 12 is a perspective view of another device for supporting the receivers.
Figure 13:
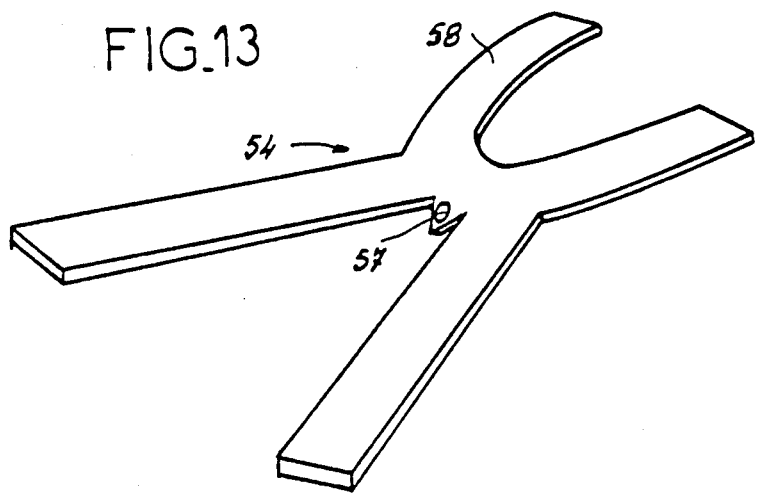
FIG. 13 is a perspective view of a fork for taking an impression, designed to be used in association with the device in FIG. 12.

FIG. 12 shows yet another device for supporting the sensors. In this device, the headpiece 2 is fitted with two clamps 48 arranged at the level of the ears of the patient, and permitting an adjustment, in terms of sliding and in rotation, of the two branches 49 of a cradle 50 whose central part, arranged in line with the face of the patient, is fitted with two clamps 52 each designed for the fitting, with adjustment in terms of sliding and in translation, of a rod 53 at the free end of which a sensor 6 is mounted.

The means for locking the clamps 48 and 52 can be purely mechanical or else pneumatic or hydraulic, which makes it possible to leave the elements completely free until the moment of their locking. In order to permit exploitation of the data obtained on a traditional mechanical articulator, the device according to the invention also comprises a special fork 54 on which the patient will close his teeth, this fork making it possible not only to position the plaster models 55 on an articulator 56, as shown in FIG. 17, but also to achieve the fixation of the diodes on the teeth of the patient.

To this end, the fork 54 comprises, as shown in FIG. 14, a cavity 57 in which the device 15, 16 for fixation of the diodes on the teeth is designed to be engaged. The plate 58 of the fork is covered on its two surfaces with a hard impression paste, and the fork is introduced into the mouth of the patient.

The patient grips the plate between his teeth and marks the impression of his teeth on the paste, the fixation of the diode support 15, 16 being effected at the same time, as well as the adjustment of the position of the sensors 6. At this point, it is possible to establish the position of the cameras, the diodes and the tooth impressions relative to the axis of rotation of the jaws, which corresponds to the axis passing through the clamps 48.

In order to modify the occlusal coordinates of a modeled surface, it is necessary to establish the position of the future prosthesis relative to the diodes in the case of the application of the device to the production of a prosthesis.

To this end, as shown in FIG. 15, the plate 58 of the fork 54 can be made of a transparent material and comprise an indicator system 59 obtained by marking or by engraving.

It is also possible, by virtue of the device according to the invention, to establish the exact height and position of the Frankfort plane, the plane passing through the mouth at the level of the base of the nose and through the axis of the ears, relative to the fork 54.

To this end, the device comprises a cradle 60 fixed on the two clamps 48, of which the branches are oriented parallel to the facial reference plane and of which the central part is fitted with a substantially vertical rod 62 comprising a member 63 for measuring the position of the fork 54 relative to this plane.

The determination of the position of these points, provided by the device according to the invention which is then used as an electronic articulator, makes it possible to position the plaster impression models of the patient on the fork, to set the fork and the impressions in a traditional articulator 56 according to the conventional methods known at present, and to adjust the values of this articulator (Bennett angle, condylar slope, cusp angle ...) taking into account the values supplied directly by the device according to the invention. This technique makes it possible to benefit, for the adjustment of the articulator, from a measurement carried out in a very accurate manner by electronic means.

As emerges from the above text, the invention brings a considerable improvement to the existing art by providing a device of simple design, and of very reliable functioning, affording a wide range of possible uses, while at the same time being very easy for the practitioner to use.

We claim:

1. A device for measuring and analyzing movements of a part of a human head of a subject, which comprises:
   a set of three light emitting diodes fixed in a removable manner on said part of said head whose movement is to be analyzed, the three light emitting diodes being arranged at the three points of a triangle on a common rigid element;
   two sensors designed to follow the movements of the diodes and mounted on a fixed support in such a way that the diodes are located in fields of view of said sensors;
   means for mounting said support on the head of the subject; and
   means for controlling the lighting of the diodes, the functioning of the sensors and the processing of the data supplied by the latter.

2. The device as claimed in claim 1, wherein the light emitting diodes emit in the infrared range and have an angle of emission of the order of 180°.

3. The device as claimed in claim 1, which has synchronization means providing for the successive lighting of the three diodes for brief intervals of time and for the simultaneous functioning of the sensors.

4. The device as claimed in claim 1, which comprises two signal-shaping stages permitting preparation of the data and transmission thereof for digitalization, a digitalization stage providing for the analog-digital conversion of the signal, under the control of the synchronization means, and a storage stage permitting storage of the data and visual display thereof on a graphic monitor.

5. The device as claimed in claim 4, wherein, in the case of the measurement and analysis of the mandibular movements, the means for processing the data comprise a stage permitting transformation of the curves analyzed on the two planes of the sensors in projection onto the three planes used in dentistry: the horizontal plane or occlusal plane, the frontal plane and the sagittal plane.

6. The device as claimed in claim 1, wherein the angle formed by the axes of the two sensors is between 35° and 120°.

7. The device as claimed in claim 6, wherein the angle formed by the axes of the two sensors is 90°.

8. The device as claimed in claim 1, wherein the three light emitting diodes are mounted in a definitive manner on a single rigid support designed to be fixed in a removable manner on the body part whose movement is to be analyzed.

9. The device as claimed in claim 8, which, in the case of the measurement and analysis of the mandibular movements, comprises a first support designed to be fixed in a removable manner on a tooth, for example by means of a photopolymerizable cement, and to receive the rigid support bearing the diodes.

10. The device as claimed in claim 1, which, in the case of the measurement and analysis of the mandibular movements, comprises a headpiece fitted with at least one arm bearing the two sensors, with the possibility of adjustment of the distance and inclination of the sensors relative to the diodes.

11. The device as claimed in claim 10, wherein the headpiece is fitted with two clamps which, arranged at the level of the ears of the patient, permit an adjustment in terms of sliding and in rotation of the two branches of a cradle of which the central part is arranged in line with the face of the patient, this central part being fitted with two clamps of axes orthogonal to the first clamps cited, each designed for the fitting, with adjustment in terms of sliding and in rotation, of a rod at the free end of which is mounted a sensor.

12. The device as claimed in claim 11, wherein the two clamps, situated at the level of the ears of the patient, are fitted with a cradle of which the branches are oriented parallel to the facial reference plane and of which the central part is fitted with a vertical rod fitted with a member for measuring the distance between the cradle and the fork.

13. The device as claimed in claim 10, wherein the means for adjustment and locking of the rods supporting the sensor are mechanical.

14. The device as claimed in claim 10, wherein the means for locking the rods supporting the sensor are hydraulic.

15. The device as claimed in claim 10, which comprises a sound sensor permitting determination of the moment at which the teeth of the patient come into contact.

16. The device as claimed in claim 10, which comprises a fork of which one end in plate form is covered, on its two surfaces, with hard impression paste, and which is equipped, on one of its surfaces and set back from the plate, with a cavity bearing the support of the diodes, this fork being designed to be introduced into the mouth of the patient to achieve the fixation of the diodes and the taking of the impression, while the adjustment of the sensors is carried out.

17. The device as claimed in claim 16, wherein the fork is made of a transparent material and comprises an indicator system.

* * * * *